USOO5624942A

United States Patent [19]

Kanno et al.

[11] Patent Number: 5,624,942
[45] Date of Patent: Apr. 29, 1997

[54] 2-PHENOXY-6-THIENYLMETHYLOXYPYRIDINE DERIVATIVE AND HERBICIDAL COMPOSITION CONTAINING SAME

[75] Inventors: Hisashi Kanno; Youichi Kanda; Susumu Shimizu; Yoshikazu Kubota; Tsutomu Sato; Masato Arahira, all of Iwaki, Japan

[73] Assignee: Kureha Kagaku Kogyo Kabushiki Kaisha, Japan

[21] Appl. No.: 503,903

[22] Filed: Jul. 18, 1995

[30] Foreign Application Priority Data

Jul. 18, 1994 [JP] Japan ................................ 6-188730
Feb. 4, 1995 [JP] Japan ................................ 7-039082

[51] Int. Cl.$^6$ ........................ C07D 405/12; A61K 31/44
[52] U.S. Cl. ........................... 514/336; 546/280.4
[58] Field of Search ........................ 546/280.4; 514/336

[56] References Cited

FOREIGN PATENT DOCUMENTS 0272533  6/1988  European Pat. Off. .......... 546/24
0572093  12/1993  European Pat. Off. .......... 546/288

OTHER PUBLICATIONS

J. Chem. Soc. (B), 1967, 758–761, "Potentially Tautomeric Pyridines. Part IX." by Katritzky et al.
Chem. Ber. 122 (1989) 589–591 "4,4'-Donor-substituierte und 6,6'-difunktionalsietre 2,2'-Bipyridine" by Neumann et al.
Roczniki Che., 33, (1956) 387–396, Chem. Abstr.
Rec. Trav. Chem. 64, (1945) 30–34, Chem. Abstr.

Primary Examiner—Alan L. Rotman
Attorney, Agent, or Firm—Parkhurst, Wendel & Burr, L.L.P.

[57] ABSTRACT

A 2-phenoxy-6-thienylmethyloxypyridine derivative represented by the formula (I):

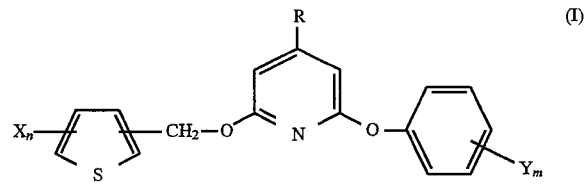

wherein R represents hydrogen, a halogen, cyano, $C_1$–$C_4$ alkyl, $C_1$–$C_4$ alkoxy, $C_1$–$C_4$ alkylthio, $C_1$–$C_4$ haloalkyl, $C_1$–$C_4$ alkylamino, or di ($C_1$–$C_4$ alkyl) amino;

each X, which may be identical or different if n is greater than 1, represents a halogen, $C_1$–$C_4$ alkyl, $C_1$–$C_4$ alkoxy, $C_1$–$C_4$ alkylthio, or $C_1$–$C_4$ haloalkyl;

each Y, which may be identical or different if m is greater than 1, represents a halogen, $C_1$–$C_4$ alkyl, $C_1$–$C_4$ alkoxy, $C_1$–$C_4$ alkylthio, $C_1$–$C_4$ haloalkyl, $C_1$–$C_4$ haloalkoxy, or $C_1$–$C_4$ haloalkylthio;

m represents an integer of 0 to 5; and n represents an integer of 0 to 3, which is useful as a herbicide.

4 Claims, No Drawings.

2-PHENOXY-6-THIENYLMETHYLOXYPYRIDINE DERIVATIVE AND HERBICIDAL COMPOSITION CONTAINING SAME

BACKGROUND OF THE INVENTION

The present invention relates to a 2-phenoxy-6-thienylmethyloxypyridine derivative, a process for producing the derivative and a herbicidal composition containing the derivative as an active ingredient.

It has been demanded a herbicide having superior herbicidal activity, such as a reliable herbicidal effect at such a low application dose that the residual amount in the environment advantageously decreases, good selectivity between crops and weeds regardless of environmental condition changes, and low phytotoxicity to the succeeding crop cultivated in a double cropping system.

The present invention has been achieved for the purpose of meeting the existing demands as set forth above. The object of the present invention is, therefore, to provide a novel compound having herbicidal activity, a process for producing the compound and a novel herbicidal composition containing the compound as an active ingredient.

The present inventors, with a view to discover a novel industrially useful pyridine derivative, have conducted extensive researches and have found that a novel 2-phenoxy-6-thienylmethyloxypyridine derivative which has not been disclosed in the publications has high herbicidal activity. Based on this finding, the present invention has been accomplished.

SUMMARY OF THE INVENTION

In a first aspect of the present invention, there is provided a 2-phenoxy-6-thienylmethyloxypyridine derivative represented by the formula (I):

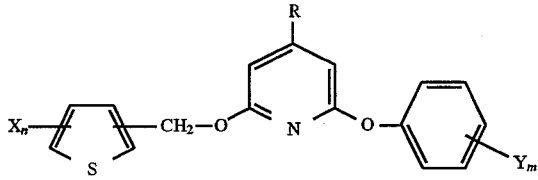

wherein R represents hydrogen, a halogen, cyano, $C_1$–$C_4$ alkyl, $C_1$–$C_4$ alkoxy, $C_1$–$C_4$ alkylthio, $C_1$–$C_4$ haloalkyl, $C_1$–$C_4$ alkylamino, or di ($C_1$–$C_4$) amino;
each X, which may be identical or different if n is greater than 1, represents a halogen, $C_1$–$C_4$ alkyl, $C_1$–$C_4$ alkoxy, $C_1$–$C_4$ alkylthio, or $C_1$–$C_4$ haloalkyl;
each Y, which may be identical or different if m is greater than 1, represents a halogen, $C_1$–$C_4$ alkyl, $C_1$–$C_4$ alkoxy, $C_1$–$C_4$ alkylthio, $C_1$–$C_4$ haloalkyl, $C_1$–$C_4$ haloalkoxy, or $C_1$–$C_4$ haloalkylthio;
m represents an integer of 0 to 5; and
n represents an integer of 0 to 3.

In a second aspect of the present invention, there is provided a process for producing a 2-phenoxy-6-thienylmethyloxypyridine derivative of the formula (I):

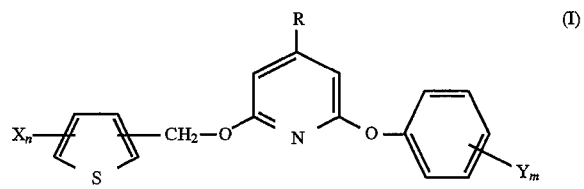

wherein R represents hydrogen, a halogen, cyano, $C_1$–$C_4$ alkyl, $C_1$–$C_4$ alkoxy, $C_1$–$C_4$ alkylthio, $C_1$–$C_4$ haloalkyl, $C_1$–$C_4$ alkylamino, or di($C_1$–$C_4$ alkyl)amino;
each X, which may be identical or different if n is greater than 1, represents a halogen, $C_1$–$C_4$ alkyl, $C_1$–$C_4$ alkoxy, $C_1$–$C_4$ alkylthio, or $C_1$–$C_4$ haloalkyl;
each Y, which may be identical or different if m is greater than 1, represents a halogen, $C_1$–$C_4$ alkyl, $C_1$–$C_4$ alkoxy, $C_1$–$C_4$ alkylthio, $C_1$–$C_4$ haloalkyl, $C_1$–$C_4$ haloalkoxy, or $C_1$–$C_4$ haloalkylthio;
m represents an integer of 0 to 5; and
n represents an integer of 0 to 3, which process comprises reacting a 2-halogeno-6-thienylmethyloxypyridine derivative of the formula (II):

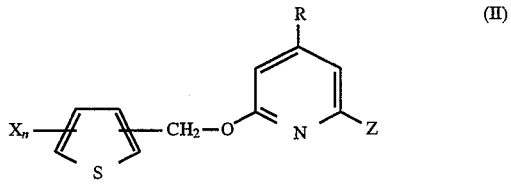

wherein R, X, and n are as defined above; and Z represents a halogen, with an unsubstituted or substituted phenol of the formula (III):

wherein Y and m are as defined above.

In a third aspect of the present invention, there is provided a herbicidal composition containing as an active ingredient a 2-phenoxy-6-thienylmethyloxypyridine derivative of the formula (I):

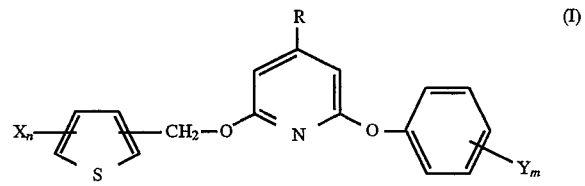

wherein R represents hydrogen, a halogen, cyano, $C_1$–$C_4$ alkyl, $C_1$–$C_4$ alkoxy, $C_1$–$C_4$ alkylthio, $C_1$–$C_4$ haloalkyl, $C_1$–$C_4$ alkylamino, or di ($C_1$–$C_4$) amino;
each X, which may be identical or different if n is greater than 1, represents a halogen, $C_1$–$C_4$ alkyl, $C_1$–$C_4$ alkoxy, $C_1$–$C_4$ alkylthio, or $C_1$–$C_4$ haloalkyl;
each Y, which may be identical or different if m is greater than 1, represents a halogen, $C_1$–$C_4$ alkyl, $C_1$–$C_4$ alkoxy, $C_1$–$C_4$ alkylthio, $C_1$–$C_4$ haloalkyl, $C_1$–$C_4$ haloalkoxy, or $C_1$–$C_4$ haloalkylthio;
m represents an integer of 0 to 5; and
n represents an integer of 0 to 3, and an adjuvant.

DETAILED DESCRIPTION OF THE INVENTION

In the definition of each substituent in the 2-phenoxy-6-thienylmethyloxypyridine derivative of the formula (I), the substituents defined by the generic terms respectively include preferred substituents as set forth below.

With respect to R, a halogen includes fluorine, chlorine, and bromine; $C_1$–$C_4$ alkyl includes methyl, ethyl, and 1-methylethyl; $C_1$–$C_4$ alkoxy includes methoxy, ethoxy, and (1-methylethyl)oxy; $C_1$–$C_4$ alkylthio includes methylthio and ethylthio; $C_1$–$C_4$ haloalkyl includes trifluoromethyl; $C_1$–$C_4$ alkylamino includes methylamino; and di($C_1$–$C_4$ alkyl)amino includes dimethylamino.

With respect to X, a halogen includes fluorine, chlorine, and bromine; $C_1$–$C_4$ alkyl includes methyl, ethyl, and 1-methylethyl; $C_1$–$C_4$ alkoxy includes methoxy, ethoxy, and (1-methylethyl)oxy; $C_1$–$C_4$ alkylthio includes methylthio, ethylthio, and (1-methylethyl)thio; and $C_1$–$C_4$ haloalkyl includes trifluoromethyl.

With respect to Y, a halogen includes fluorine, chlorine, and bromine; $C_1$–$C_4$ alkyl includes methyl, ethyl, and 1-methylethyl; $C_1$–$C_4$ alkoxy includes methoxy, ethoxy, and (1-methylethyl)oxy; $C_1$–$C_4$ alkylthio includes methylthio, ethylthio, and (1-methylethyl)thio; $C_1$–$C_4$ haloalkyl includes trifluoromethyl; $C_1$–$C_4$ haloalkoxy includes difluoromethoxy and trifluoromethoxy; and $C_1$–$C_4$ haloalkylthio includes trifluoromethylthio.

Preferably, the substituents R, X and Y are as follows. R preferably represents methoxy, cyano, dimethylamino, methylamino, chlorine, or methyl. X preferably represents 'unsubstituted' (n=0), methyl, bromine, or chlorine. Y preferably represents trifluoromethyl, trifluoromethoxy, trifluoromethylthio, or difluoromethoxy.

As for the preferred range of integers m and n, m is 0 to 3 and n is 0 to 2.

Examples of the 2-phenoxy-6-thienylmethyloxypyridine derivative of the formula (I) which has the combination of the preferred substituents and integers as described above are shown in the Table 1 below.

TABLE 1

| No.  | R         | $X_n$[1)]      | $Y_M$[2)]   | A[3)] |
|------|-----------|----------------|-------------|-------|
| I-1  | H         | Unsubstituted  | 3-Cl        | 3     |
| I-2  | H         | Unsubstituted  | 3-$CH_3$    | 3     |
| I-3  | H         | Unsubstituted  | 3-$CF_3$    | 2     |
| I-4  | H         | Unsubstituted  | 3-$CF_3$    | 3     |
| I-5  | H         | Unsubstituted  | 3-$OCHF_2$  | 3     |
| I-6  | H         | Unsubstituted  | 3-$OCF_3$   | 3     |
| I-7  | H         | 5-$CH_3$       | 3-$CF_3$    | 2     |
| I-8  | Cl        | Unsubstituted  | 3-$CF_3$    | 3     |
| I-9  | CN        | Unsubstituted  | 3-$CF_3$    | 3     |
| I-10 | $CH_3$    | Unsubstituted  | 3-$CF_3$    | 3     |
| I-11 | $OCH_3$   | Unsubstituted  | Unsubstituted | 3   |
| I-12 | $OCH_3$   | Unsubstituted  | 3,4-$Cl_2$  | 3     |
| I-13 | $OCH_3$   | Unsubstituted  | 3-$CF_3$    | 3     |
| I-14 | $OCH_3$   | Unsubstituted  | 3,5-$(CF_3)_2$ | 3  |
| I-15 | $OCH_2CH_3$ | Unsubstituted | 3-$CF_3$    | 3     |
| I-16 | $OCH_3$   | Unsubstituted  | 3-$SCF_3$   | 3     |
| I-17 | $OCH_3$   | Unsubstituted  | 3-$OCHF_2$  | 3     |
| I-18 | $OCH_3$   | 4-Br           | 3-$CF_3$    | 2     |
| I-19 | $OCH_3$   | 5-Br           | 3-$CF_3$    | 2     |
| I-20 | $OCH_3$   | 3-Me           | 3-$CF_3$    | 2     |
| I-21 | $OCH_3$   | 5-Me           | 3-$CF_3$    | 2     |
| I-22 | $OCH_3$   | 2,5-$Br_2$     | 3-$CF_3$    | 3     |
| I-23 | $OCH_3$   | 2,5-$(CH_3)_2$ | 3-$CF_3$    | 3     |
| I-24 | $OCH_3$   | 5-$SCH_3$      | 3-$CF_3$    | 3     |
| I-25 | $OCH_3$   | 5-$CF_3$       | 3-$CF_3$    | 3     |
| I-26 | $SCH_3$   | Unsubstituted  | 3-$CF_3$    | 3     |
| I-27 | $CF_3$    | Unsubstituted  | 3-$CF_3$    | 3     |
| I-28 | $NHCH_3$  | Unsubstituted  | 3-$CF_3$    | 3     |
| I-29 | $N(CH_3)_2$ | Unsubstituted | 3-$CF_3$    | 3     |

[1)]FIGS. preceding a hyphen symbol (-) represent the bonded position, whereas symbols following the hyphen symbol (-) represent the substituent and the number thereof when the substituent bond to 2 or more positions. For example, 5-$CH_3$ in the compound (I-6) means that methyl bonds to the position 5 on the thiophene ring. Similarly, 5-$SCH_3$ in the compound (I-24) means that methylthio bonds to the position 5 on the thiophene ring and 2,5-$Br_2$ in the compound (I-22) means that two atoms of bromine bond to the positions 2 and 5.

[2)]FIGS. preceding a hyphen symbol (-) represent the bonded position, whereas symbols following the hyphen symbol (-) represent the substituent and the number thereof when the substituents bond to 2 or more positions. For example, 3-Cl in the compound (I-1) means that chlorine bonds to the position 3 (meta position) on the benzene ring. Similarly, 3-$OCF_3$ in the compound (I-6) means that trifluoromethoxy is bonded to the position 3 (meta position) on the benzene ring, and 3,4-$Cl_2$ in the compound (I-12) means that two atoms of chlorine bond to the positions 3 and 4.

[3)]A represents the bonded position on the thiophene ring of the carbon atom of the $CH_2O$ connecting the thiophene ring to the pyridine ring.

The 2-phenoxy-6-thienylmethyloxypyridine derivative of the formula (I) (Compound (I)) may be synthesized in accordance with the Reaction scheme I set forth in the following.

Reaction Scheme I

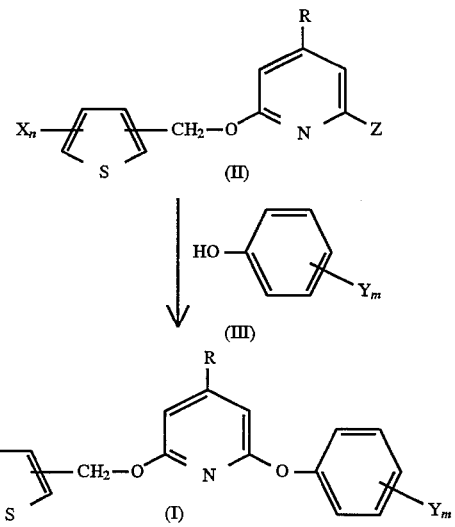

wherein R, X, Y, n, and m are as defined above and Z represent a halogen.

The 2-halogeno-6-thienylmethyloxypyridine derivative of the formula (II) may be synthesized in accordance with the Reaction scheme II.

Reaction Scheme II

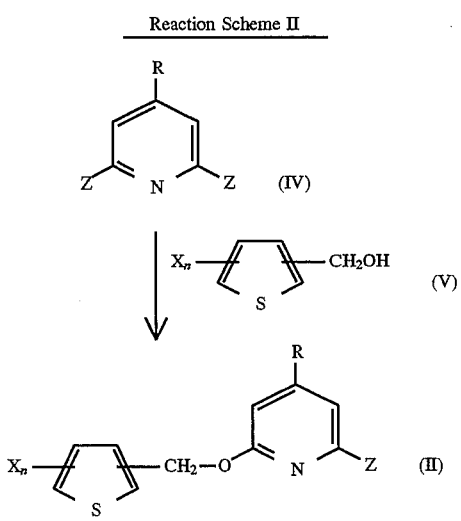

wherein R, X, and n are as defined above and Z presents a halogen, and each Z in the formula (IV) may be identical or different.

Examples of the unsubstituted or substituted phenol of the formula (III) which may be used for the production of the compounds (I) are as follows: phenol, meta-cresol, meta-chlorophenol, 3,4-dichlorophenol, meta-trifluoromethylphenol, 3,5-di(trifluoromethyl)phenol, 3-(difluoromethoxy)phenol, meta-trifluoromethoxyphenol, and 3-(trifluoromethylthio)phenol.

Examples of the unsubstituted or substituted thiophenemethanol of the formula (V) are as follows: 2-thiophenemethanol, 3-thiophenemethanol, 4-bromo-2-thiophenemethanol, 5-bromo-2-thiophenemethanol, 2,5-dibromo-3-thiophenemethanol, 3-methyl-2-thiophenemethanol, 5-methyl-2-thiophenemethanol, 5-methyl-3-thiophenemethanol, 2,5-dimethyl-3-thiophenemethanol, 5-methylthio-3-thiophenemethanol, and 5-trifluoromethyl-3thiophenemethanol.

The unsubstituted or substituted thiophenemethanol of the formula (V) and the unsubstituted or substituted phenol of the formula (III) may be commercially available or may be easily obtained in accordance with existing techniques.

The 2,6-dihalogeno-4-substituted-pyridine of the formula (IV) may also be commercially available or may be easily obtained in accordance with existing techniques.

For example, 2,6-dichloro-4-cyanopyridine is described in the Roczniki Chem. 1959, 33, 387 and others. 2,6-Dichloro-4-methoxypyridine and 2,6-dibromo-4-methoxypyridine are described respectively in the J. Chem. Soc. B 1967, (8), 758 and Chem. Ber. 1989, 122(3), 589.

Further, the 2,6-dihalogeno-4-substituted-pyridine of the formula (IV) may be obtained by substituting a suitable group for nitro of 2,6-dichloro-4-nitropyridine disclosed in EP 053306 A through nucleophilic displacement by using $C_1$–$C_4$ alkanol such as methyl alcohol, ethyl alcohol, and 1-methylethyl alcohol.

2,6-Dichloro-4-($C_1$–$C_4$ alkylthio)pyridine may be obtained by substituting a suitable group for nitro of 2,6-dichloro-4-nitropyridine through nucleophilic displacement by using $C_1$–$C_4$ alkanethiol such as methanethiol and ethanethiol.

2,6-Dichloro-4-($C_1$–$C_4$ alkylamino)pyridine may be obtained by substituting a suitable group for nitro of 2,6-dichloro-4-nitropyridine through nucleophilic displacement by using $C_1$–$C_4$ alkylamine such as methylamine and ethylamine.

2,6-Dichloro-4-[di($C_1$–$C_4$ alkyl)amino]pyridine may be obtained by substituting a suitable group for nitro of 2,6-dichloro-4-nitropyridine through nucleophilic displacement by using di($C_1$–$C_4$ alkyl)amine such as dimethylamine and diethylamine.

The 2,6-dichloro-4-[di($C_1$–$C_4$ alkyl)amino]pyridine may be also obtained by alkylating nitrogen of $C_1$–$C_4$ alkylamino of 2,6-dichloro-4-($C_1$–$C_4$ alkylamino)pyridine with $C_1$–$C_4$ alkyl halide such as methyl iodide, ethyl iodide, and propyl bromide. The method is suited to production of the compound having dialkylamino wherein each alkyl is different.

Further, the 2,6-dichloro-4-[di($C_1$–$C_4$ alkyl)amino] pyridine may be obtained by dialkylating amino of 4-amino-2,6-dichloropyridine. This method is suited to production of the compound having dialkylamino wherein each alkyl is identical.

The 2,6-dihalogeno-4-substituted-pyridine of the formula (IV) wherein the halogen represented by the symbol Z is chlorine, bromine, or iodine is preferably used.

According to the production process of the present invention, every reaction may be advantageously conducted in a solvent or a mixture of solvents. Examples of the solvents are set forth below:

aromatic hydrocarbons such as benzene, toluene, xylene, and methylnaphthalene;

aliphatic hydrocarbons such as petroleum ether, pentane, hexane, heptane, and methylcyclohexane;

halogenated hydrocarbons such as methylene chloride, chloroform, carbon tetrachloride, and chlorobenzene;

amides such as dimethylformamide, dimethylacetamide, and N-methyl-2-pyrrolidinone;

ethers such as diethyl ether, dimethoxyethane, diisopropyl ether, tetrahydrofuran, diglyme, and dioxane;

as well as others including carbon disulfide, acetonitrile, ethyl acetate, pyridine, dimethyl sulfoxide, hexamethylphosphoric amide, and the like.

When the production process of the present invention is carried out in a solvent, the solvent may be used alone or in combination of two or more. A mixture of the solvents incapable of forming a homogeneous phase may also be used. In this case, the reaction may preferably be conducted in the presence of a phase transfer catalyst such as a conventional quaternary ammonium salt or crown ether.

Since the production process of the present invention is based on nucleophilic displacement at the carbon atom on the pyridine ring, the reaction may preferably be conducted in the presence of a base. Further, copper(I) chloride, copper (I) bromide, and copper(I) iodide are preferably used together with the base. Examples of the base are basic compounds such as follows:

alkaline metal hydrogen carbonates such as potassium hydrogen carbonate and sodium hydrogen carbonate;

alkaline metal carbonates such as potassium carbonate and sodium carbonate;

alkaline metal hydroxides such as potassium hydroxide and sodium hydroxide;

alkaline metals such as lithium, sodium and potassium, and alkaline earth metals such as magnesium;

alkaline metal alkoxides such as sodium methoxide, sodium ethoxide, and potassium t-butoxide;

alkaline metal hydrides such as sodium hydride and potassium hydride;

alkaline earth metal hydrides such as calcium hydride;

organic alkaline metal compounds such as methyl lithium, ethyl lithium, n-butyl lithium, and phenyl lithium;

Grignard reagents such as methylmagnesium iodide, ethylmagnesium bromide, and n-butylmagnesium bromide;

organic copper compounds prepared from organic alkaline metal compounds or Grignard reagents and copper (I) salts; and alkaline metal amides such as lithium diisopropylamide.

The reaction conditions for each of the Reaction schemes I and II may be suitably selected, and these reactions are usually conducted respectively at the temperature in the range of 1° to 200° C. for 0.5 to 30 hours and at the temperature in the range of 1° to 200° C. for 0.5 to 10 hours, if necessary, under pressurization.

Although the Compound (I) of the present invention may be applied as it is, it is generally applied after formulated with an adjuvant into various forms of compositions such as powders, wettable powders, granules or emulsifiable concentrates.

If formulated, the composition contains one or more of the compounds (I) at an amount of 0.to 95 % by weight, preferably 0.5 to 90 % by weight, more preferably 2 to 70 % by weight.

Among adjuvants including carriers (diluents) and surface active agents, suitable solid carriers are talc, kaolin, bentonite, diatomaceous earth, white carbon, clay, and the like. Suitable liquid diluents are water, xylene, toluene, chlorobenzene, cyclohexane, cyclohexanone, acetone, dimethylsulfoxide, dimethylformamide, alcohol, and the like. Surface active agents may be properly selected depending upon their effects, and suitable emulsifying agents include polyoxyethylene alkylaryl ether, polyoxyethylene sorbitan monolaurate, and the like. Suitable dispersing agents include lignin sulfonate, dibutylnaphthalene sulfonate, and the like. Suitable wetting agents are alkyl sulfonates, alkylphenyl sulfonates, and the like.

The above mentioned compositions include those which are to be applied as such and those which are to be applied after diluted to a proper concentration by using a diluent such as water. When diluted, the Compound (I) is contained preferably at a concentration of 0.001 to 1.0% by weight. Application dose of the Compound (I) of the present invention is usually 0.01 to 10 kg/ha, preferably 0.05 to 5 kg/ha.

The concentrations and the application doses described above are varied depending on dosage forms, time of application, way of application, application sites, crops to be treated and the like. Thus, modifications thereof are possible without limited to the above defined range. Further, the Compound (I) of the present invention may be used in combination with other active ingredients such as fungicides, insecticides, acaricides and herbicides.

EXAMPLES

The 2-phenoxy-6-thienylmethyloxypyridine derivative of the present invention, the production process and the use thereof will be more specifically described by way of synthesis examples, formulation examples and test examples set forth in the following.

It will be also understood that the present invention should be considered as not limited to these examples without departing from the scopes thereof.

SYNTHESIS EXAMPLE 1

Synthesis of 2-(2-thienylmethyloxy)-6-(meta-trifluoromethylphenoxy)pyridine (I-3)
(1) Synthesis of an intermediate, 2-chloro-6-(2-thienylmethyloxy)pyridine To a solution containing 2-thiophenemethanol (1.5 g, 0.0135×1.0 mol) and sodium hydride (0.58 g, (ca.60% in mineral oil), 0.0135×1.1 mol) in tetrahydrofuran, 2,6-dichloropyridine (2.0 g, 0.0135 mol) was added and the resultant solution was refluxed for about 2 hours. The reaction solution was partitioned between ethyl acetate and aqueous saturated sodium hydrogen carbonate. The obtained organic layer was washed with aqueous saturated sodium chloride, dried over anhydrous sodium sulfate and thereafter, concentrated and purified on a silica gel column to obtain the end product.

Yield: 2.69 g (89%). Oily product.
$^1$H-NMR (60 MHz, CDCl$_3$, δ): 5.45(2H, s), 7.3–7.6(6H, complex).

(2) Synthesis of 2-(2-thienylmethyloxy)-6-(meta-trifluoromethylphenoxy)pyridine from the intermediate To a solution containing meta-trifluoromethylphenol (3.62 g, 0.0045×5.0 mol), sodium hydride (0.36 g, (Ca.60% in mineral oil), 0.0045×2.0 mol) and CuI (0.42 g, 0.0045× 0.5 mol) in dimethylformamide, 2-chloro-6-(2-thienylmethyloxy)pyridine (1.0 g, 0.0045 mol) was added and the resultant solution was refluxed for about 3 hours. Additional sodium hydride (0.36 g, (60% in mineral oil), 0.0045×2.0 mol) was added thereto and the resultant solution was refluxed for another about 1 hour, thereafter the reaction solution was partitioned between ethyl acetate and aqueous saturated sodium hydrogen carbonate. The obtained organic layer was washed with aqueous saturated sodium chloride, dried over anhydrous sodium sulfate and thereafter, concentrated and purified on a silica gel column to obtain the end product.

Yield: 0.60 g (42%). Oily product.
$^1$H-NMR (60 MHz, CDCl$_3$, δ): 5.20(2H,s), 6.40(2H,d,J=7.9 Hz), 6.7–7.7(8H, complex).

SYNTHESIS EXAMPLE 2

Synthesis of 2-(3-thienylmethyloxy)-6-(meta-trifluoromethylphenoxy)pyridine (I-4)
(1) Synthesis of an intermediate, 2-chloro-6-(3-thienylmethyloxy)pyridine To a solution containing 3-thiophenemethanol (1.17 g, 0.010×1.0 mol) and sodium hydride (0.39 g, (ca.60% in mineral oil), 0.010×1.0 mol) in tetrahydrofuran, 2,6-dichloropyridine (1.5 g, 0.010 mol) was added and the resultant solution was refluxed for about 2 hours.

The reaction solution was partitioned between ethyl acetate and aqueous saturated sodium hydrogen carbonate. The obtained organic layer was washed with aqueous saturated sodium chloride, dried over anhydrous sodium sulfate and thereafter, concentrated and purified on a silica gel column to obtain the end product.

Yield: 1.94 g (87%). Oily product.
$^1$H-NMR (60 MHz, CDCl$_3$, δ): 5.29(2H,s), 6.57(1H,d,J=7.9 Hz), 6.79(1H,d,J=7.5 Hz), 7.0–7.6(4H, complex).

(2) Synthesis of 2-(3-thienylmethyloxy)-6-(meta-trifluoromethylphenoxy)pyridine pyridine from the intermediate To a solution containing meta-trifluoromethylphenol (3.62 g, 0.0045×5.0 mol), sodium hydride (0.89 g, (Ca.60% in mineral oil), 0.0045×5.0 mol) and CuI (0.42 g, 0.0045× 0.5 mol) in dimethylformamide, 2-chloro-6-(3-thienylmethyloxy)pyridine (1.0 g, 0.0045 mol) was added and the resultant solution was refluxed for about 3 hours.

Then, the reaction solution was partitioned between ethyl acetate and aqueous saturated sodium hydrogen carbonate. The obtained organic layer was washed with aqueous saturated sodium chloride, dried over anhydrous sodium sulfate and thereafter, concentrated and purified on a silica gel column to obtain the end product.

Yield: 0.71 g (50%). Oily product.

$^1$H-NMR (60 MHz, CDCl$_3$, δ): 5.06(2H,s), 6.39(1H,d,J=7.9 Hz), 6.43(1H,d,J=7.9 Hz), 6.8–7.7(8H, complex).

SYNTHESIS EXAMPLE 3

Synthesis of 4-chloro-2-(3-thienylmethyloxy)-6-(meta-trifluoromethylphenoxy)pyridine (I-8)

(1) Synthesis of an intermediate, 2,4-dichloro-6-(3thienylmethyloxy)pyridine:

To a solution of 3-thiophenemethanol (0.32 g, 0.0027×1.05 mol) in 10 ml of dry tetrahydrofuran, sodium hydride (0.13 g, (ca.60% in mineral oil), 0.0027×1.2 mol) was added. After the bubbling ceased, a solution of 2,4,6-trichloropyridine (0.49 g, 0.0027 mol) in 10 ml of dry tetrahydrofuran was added dropwise at room temperature.

Thereafter, the resultant solution was stirred for about 15 hours under reflux. Then, the solvent was distilled off and the residue was partitioned between ethyl acetate and water. The obtained organic layer was washed with aqueous saturated sodium chloride and dried over anhydrous sodium sulfate. After the solvent was distilled off, the residue was purified on a silica gel column to obtain the end product.

Yield: 0.58 g (84%). Oily product.

$^1$H-NMR (60 MHz, CDCl$_3$, δ): 5.26(2H,s), 6.57(1H,d,J=2 Hz), 6.8(1H,d,J=2 Hz), 6.9–7.3(3H, complex).

(2) Synthesis of 4-chloro-2-(3-thienylmethyloxy)-6-(meta-trifluoromethylphenoxy)pyridine from the intermediate To a solution of meta-trifluoromethylphenol (0.28 g, 0.0018×1.0 mol) in 10 ml of dry N,N-dimethylacetamide, sodium hydride (0.077 g, (ca.60% in mineral oil), 0.0018×1.1 mol) was added. After the bubbling ceased, a solution of 2,4-dichloro-6-(3-thienylmethyloxy)pyridine (0.46 g, 0.0018 mol) in 10 ml of dry N,N-dimethylacetamide was added dropwise and the resultant solution was stirred for about 7 hours at the temperature of 160° to 170° C. After allowed to cool, water was added to the reaction solution, then the mixture was partitioned by using ethyl acetate. The obtained organic layer was washed with aqueous saturated sodium chloride and dried over anhydrous sodium sulfate. The solvent was distilled off, then the residue was purified successively on silica gel column chromatography and on reversed phase column chromatography (Lobar column, Lichroprep RP-18, 40–63 μm, elution solvent: CH$_3$CN/H$_2$O=7/3(v/v)), whereby the end product was obtained.

Yield: 0.10 g (15%). Oily product. $^1$H-NMR (60 MHz, CDCl$_3$, δ): 5.00(2H,s), 6.42(2H,s), 6.7–7.5(7H, complex).

SYNTHESIS EXAMPLE 4

Synthesis of 4-cyano-2-(3-thienylmethyloxy)-6-(meta-trifluoromethylphenoxy)pyridine (I-9)

(1) Synthesis of an intermediate, 2-chloro-4-cyano-6-(3-thienylmethyloxy)pyridine Sodium hydride (0.24 g (ca.60% in mineral oil), 0.006×1.0 mol) was suspended in 20 ml of N-methyl-2-pyrrolidinone, and 3-thiophenemethanol (0.69 g, 0.006×1.0 mol) was added thereto and the resultant solution was stirred for about 30 minutes at room temperature. The resultant mixture was cooled to 4° C. with iced water, then 4-cyano-2,6-dichloropyridine (1.04 g, 0.006 mol) was added thereto and stirred for about 1.5 hour while cooling with iced water.

After stirred for another about 1.5 hours, the reaction solution was partitioned between ethyl acetate and water. The obtained organic layer was washed with aqueous saturated sodium chloride, dried over anhydrous sodium sulfate and thereafter, concentrated and purified on a silica gel column to obtain the end product.

Yield: 0.94 g (63%). Oily product.

$^1$H-NMR (60 MHz, CDCl$_3$, δ): 5.30(2H,s), 6.78(1H, s), 6.97(1H,s), 6.9–7.4(3H, complex).

(2) Synthesis of 4-cyano-2-(3-thienylmethyloxy)-6-(meta-trifluoromethylphenoxy)pyridine from the intermediate 2-Chloro-4-cyano-6-(3-thienylmethyloxy)pyridine (0.79 g, 0.00315 mol) and meta-trifluoromethylphenol (0.57 g, 0.00315×1.1 mol) were dissolved in 20 ml of N-methyl-2-pyrrolidinone, and anhydrous potassium carbonate (0.48 g, 0.00315×1.1 mol) was added thereto, and the resultant solution was stirred for about 4 hours at about 100° C.

Then, the reaction solution was partitioned between ethyl acetate and water. The obtained organic layer was washed with aqueous saturated sodium chloride, dried over anhydrous sodium sulfate and thereafter, concentrated and purified on silica gel column. Then the end product was obtained by recrystallization from a small amount of n-hexane.

Yield: 0.71 g (47%). Solid.

Melting point 67°–68° C.

$^1$H-NMR (60 MHz, CDCl$_3$, δ): 5.03(2H,s), 6.60(2H,s), 6.6–7.6 (7H, complex).

SYNTHESIS EXAMPLE 5

Synthesis of 4-methyl-2-(3-thienylmethyloxy)-6-(meta-trifluoromethylphenoxy)pyridine (I-10)

(1) Synthesis of an intermediate, 2-chloro-4-methyl-6-(3-thienylmethyloxy)pyridine To a solution containing 3-thiophenemethanol (0.78 g, 0.0062×1.1 mol) and sodium hydride (0.26 g, (ca.60% in mineral oil), 0.0062×1.05 mol) in tetrahydrofuran, 2,6-dichloro-4-methylpyridine (1.0 g, 0.0062 mol) was added, and the resultant solution was refluxed for about 1 hour.

Then, the reaction solution was partitioned between ethyl acetate and aqueous saturated sodium hydrogen carbonate. The obtained organic layer was washed with aqueous saturated sodium chloride, dried over anhydrous sodium sulfate and thereafter, concentrated and purified on silica gel column to obtain the end product.

Yield: 1.21 g (82%). Oily product.

$^1$H-NMR (60 MHz, CDCl$_3$, δ): 2.20(3H,s), 5.26(2H,s), 6.38(1H,s), 6.64(1H,s), 6.9–7.4(3H, complex).

(2) Synthesis of 4-methyl-2-(3-thienylmethyloxy)-6-(meta-trifluoromethylphenoxy)pyridine from the intermediate To a solution containing meta-trifluoromethylphenol (1.70 g, 0.0021×5.0 mol) and sodium hydride (0.42 g, (ca.60% in mineral oil), 0.0021×5.0 mol) in dimethylformamide, 2-chloro-4-methyl-6-(3-thienylmethyloxy)pyridine (0.5 g, 0.0021 mol) and CuI (0.20 g, 0.0021×0.5 mol) were successively added and the resultant solution was refluxed for about 5 hours.

Then, the reaction solution was partitioned between ethyl acetate and aqueous saturated sodium hydrogen carbonate. The obtained organic layer was washed with aqueous saturated sodium chloride, dried over anhydrous sodium sulfate and thereafter, concentrated and purified on a silica gel column to obtain the end product.

Yield: 0.34 g (45%). Oily product.

$^1$H-NMR (60 MHz, CDCl$_3$, δ): 2.23(3H,s), 5.05(2H,s), 6.25(2H,s), 6.6–7.6(7H, complex).

SYNTHESIS EXAMPLE 6

Synthesis of 4-methoxy-2-(3-thienylmethyloxy)-6-(meta-trifluoromethylphenoxy)pyridine (I-13)

(1) Synthesis of an intermediate, 2-chloro-4-methoxy-6-(3-thienylmethyloxy)pyridine To a solution containing 3-thiophenemethanol (0.45 g, 0.0033×1.2 mol) and sodium hydride (0.14 g, (ca.60% in mineral oil), 0.033×1.05 mol) in tetrahydrofuran, 2,6-dichloro-4-methoxypyridine (0.59 g, 0.0033 mol) was added and the resultant solution was refluxed for about 2 hours.

Then, the reaction solution was partitioned between ethyl acetate and aqueous saturated sodium hydrogen carbonate. The obtained organic layer was washed with aqueous saturated sodium chloride, dried over anhydrous sodium sulfate and thereafter, concentrated and purified on a silica gel column to obtain the end product.

Yield: 0.64 g (76%). Oily product.

$^1$H-NMR (60 MHz, CDCl$_3$, δ): 3.63(3H,s), 5.17(2H,s), 5.95(1H,d,J=2.0 Hz), 6.30(1H,d,J=2.0 Hz), 6.7–7.2(3H, complex).

(2) Synthesis of 4-methoxy-2-(3-thienylmethyloxy)-6-(meta-trifluoromethylphenoxy)pyridine from the intermediate To a solution containing meta-trifluoromethylphenol (1.40 g, 0.0021×4.0 mol), sodium hydride (0.25 g, (ca.60% in mineral oil), 0.0021×3.0 mol) and CuI (0.20 g, 0.0021× 0.5 mol) in dimethylformamide, 2-chloro-4-methoxy-6-(3-thienylmethyloxy)pyridine (0.54 g, 0.0021 mol) was added and the resultant solution was refluxed for about 6 hours.

Then, the reaction solution was partitioned between ethyl acetate and aqueous saturated sodium hydrogen carbonate. The obtained organic layer was washed with aqueous saturated sodium chloride, dried over anhydrous sodium sulfate and thereafter, concentrated and purified on a silica gel column to obtain the end product.

Yield: 0.39 g (49%). Oily product.

$^1$H-NMR (60 MHz, CDCl$_3$, δ): 3.65(3H,s) , 4.94(2H,s), 5.85(2H,s), 6.6–7.4(7H, complex).

SYNTHESIS EXAMPLE 7

Synthesis of 4-methylmercapto-2-(3-thienylmethyloxy)-6-(meta-trifluoromethylphenoxy)pyridine (I-26)

(1) Synthesis of an intermediate, 2-chloro-4-methylmercapto-6-(3-thienylmethyloxy)pyridine To a solution containing 3-thiophenemethanol (0.56 g, 0.0041×1.2 mol) and sodium hydride (0.17 g, (ca.60% in mineral oil), 0.0041×1.05 mol) in tetrahydrofuran, 2,6-dichloro-4-methylmercaptopyridine (0.80 g, 0. 0041 mol) was added, and the resultant solution was refluxed for about 2 hours.

Then, the reaction solution was partitioned between ethyl acetate and aqueous saturated sodium hydrogen carbonate. The obtained organic layer was washed with aqueous saturated sodium chloride, dried over anhydrous sodium sulfate and thereafter, concentrated and purified on a silica gel column to obtain the end product.

Yield: 0.74 g (66%). Oily product.

$^1$H-NMR (60 MHz, CDCl$_3$, δ): 2.33(3H,s), 5.17(2H,s), 6.24(1H,d,J=1 Hz), 6.54(1H,d,J=1 Hz), 6.7–7.3(3H, complex).

(2) Synthesis of 4-methylmercapto-2-(3-thienylmethyloxy)-6-(meta-trifluoromethylphenoxy)pyridine from the intermediate To a solution containing meta-trifluoromethylphenol (1.60 g, 0.0024×4.1 mol), sodium hydride (0.29 g, (ca.60% in mineral oil), 0.0024×3.0 mol) and CuI (0.22 g, 0.0024× 0.5 mol) in dimethylformamide, 2-chloro-4-methylmercapto-6-(3-thienylmethyloxy)pyridine (0.64 g, 0. 0024 mol) was added and the resultant solution was refluxed for about 6 hours.

Then, the reaction solution was partitioned between ethyl acetate and aqueous saturated sodium hydrogen carbonate. The obtained organic layer was washed with aqueous saturated sodium chloride, dried over anhydrous sodium sulfate and thereafter, concentrated and purified on a silica gel column to obtain the end product.

Yield: 0.46 g (49%). Oily product.

$^1$H-NMR (60 MHz, CDCl$_3$, δ): 2.33(3H,s), 4.90(2H,s), 6.12(2H,s), 6.6–7.4(7H, complex).

SYNTHESIS EXAMPLE 8

Synthesis of 2-(3-thienylmethyloxy)-4-trifluoromethyl-6-(meta-trifluoromethylphenoxy)pyridine (I-27)

(1) Synthesis of an intermediate, 2-chloro-6-(3-thienylmethyloxy)-4-trifluoromethylpyridine To a mixture prepared by adding to 3-thiophenemethanol (1.27 g, 0.0093×1.2 mol) successively tetrahydrofuran and sodium hydride (0.39 g, (ca.60% in mineral oil), 0.0093× 1.05 mol), 2,6-dichloro-4-trifluoromethylpyridine (2.0 g, 0.0093 mol) was added, and the resultant solution was refluxed for about 1 hour.

Then, the reaction solution was partitioned between ethyl acetate and aqueous saturated sodium hydrogen carbonate. The obtained organic layer was washed with aqueous saturated sodium chloride, dried over anhydrous sodium sulfate and thereafter concentrated. The concentrate was purified on a silica gel column and the starting material which was difficult to separate was distilled off by using a tubular oven, whereby the end produce was obtained.

Yield: 2.42 g (89%). Oily product.

$^1$H-NMR (60 MHz, CDCl$_3$, δ): 5.34(2H,s), 6.83(1H,s), 6.9–7.5 (4H, complex).

(2) Synthesis of 2-(3-thienylmethyloxy)-4-trifluoromethyl-6-(meta-trifluoromethylphenoxy) pyridine from the intermediate To a mixture prepared by adding to meta-trifluoromethylphenol (1.1 g, 0.0034×2.0 mol) successively dimethylformamide and sodium hydride (0.20 g, (ca.60% in mineral oil), 0.0034×1.5 mol), 2-chloro-6-(3-thienylmethyloxy)-4-trifluoromethylpyridine (1.0 g, 0.0034 mol) was added, and the resultant solution was refluxed for about 2 hours.

Then, the reaction solution was partitioned between ethyl acetate and aqueous saturated sodium hydrogen carbonate. The obtained organic layer was washed with aqueous saturated sodium chloride, dried over anhydrous sodium sulfate and thereafter concentrated. The concentrate was purified on a silica gel column and the starting material which was difficult to separate was distilled off by using a tubular oven, whereby the end product was obtained.

Yield: 1.03 g (72%). Oily product.

$^1$H-NMR (60 MHz, CDCl$_3$, δ): 5.03(2H,s), 6.63(2H,s), 6.7–7.6(7H, complex).

SYNTHESIS EXAMPLE 9

Synthesis of 4-methylamino-2-(3-thienylmethyloxy)-6-(meta-trifluoromethylphenoxy)oyridine (I-28)

(1) Synthesis of an intermediate, 2-chloro-4-methylamino-6-(3-thienylmethyloxy)pyridine To a solution of 3-thiophenemethanol (1.42 g, 0.0113×1.1 mol) in 20 ml of dry tetrahydrofuran, sodium hydride (1.35 g (ca.60% in mineral oil), 0.0113×3.0 mol) was added. After the bubbling ceased, a solution of 2,6-dichloro-4-methylaminopyridine (2.0 g, 0.0113 mol) in 30 ml of dry tetrahydrofuran was added dropwise at room temperature.

After the addition, the reaction solution was stirred for about 20 hours under reflux. Then, the solvent was distilled off and the residue was partitioned between ethyl acetate and water. The obtained organic layer was washed successively with aqueous saturated sodium hydrogen carbonate and aqueous saturated sodium chloride, then dried over anhydrous sodium sulfate. After the solvent was distilled off, the residue was purified on a silica gel column to obtain the end product.

Yield: 0.45 g (16%). Oily product.

$^1$H-NMR (60 MHz, CDCl$_3$, δ): 2.64(3H,d,J=5 Hz), 4.2 (1H,q, J=5 Hz), 5.2(2H,s), 5.6(1H,d,J=2 Hz), 6.0(1H,d,J=2 Hz), 6.9–7.3(3H, complex).

(2) Synthesis of 4-methylamino-2-(3-thienylmethyloxy)-6-(meta-trifluoromethylphenoxy) pyridine from the intermediate To a solution of meta-trifluoromethylphenol (0.81 g, 0.00125×4.0 mol) in 10 ml of dry N,N-dimethylacetamide, sodium hydride (0.25 g (ca.60% in mineral oil), 0.00125×5.0 mol) was added. After the bubbling ceased, a solution of 2-chloro-4-methylamino-6-(3-thienylmethyloxy)pyridine (0.32 g, 0.00125 mol) in 10 ml of dry N,N-dimethylacetamide was added dropwise.

Then, CuI (0.12 g, 0.00125×0.5 mol) was added thereto and the resultant solution was stirred four 24 hours at the temperature of about 170° to 180° C. After allowed to cool, the reaction solution was filtered through a glass filter covered with Celite and the filtrate was partitioned between chloroform and water. The obtained organic layer was washed successively with aqueous saturated sodium hydrogen carbonate and aqueous saturated sodium chloride, then dried over anhydrous sodium sulfate. The solvent was distilled off and the residue was purified on column chromatography (elution solvent: acetonitrile/water=7/3 (v/v), Lobar column, Lichroprep RP-18, 40–63 μm), whereby the end product was obtained.

Yield: 0.18 g (37%). Oily product.

$^1$H-NMR (60 MHz, CDCl$_3$, δ): 2.7(3H,d,J=5 Hz), 3.9–4.3 (1H,s), 5.0(2H,s) 5.6(2H,s), 6.75–7.4(7H, complex).

SYNTHESIS EXAMPLE 10

Synthesis of 4-dimethylamino-2-(3-thienylmethyloxy)-6-(meta-trifluoromethylphenoxy)pyridine (I-29)

(1) Synthesis of an intermediate, 2-chloro-4-dimethylamino-6-(3-thienylmethyloxy)pyridine To a solution of 3-thiophenemethanol (0.526 g, 0.0042×1.1 mol) in 10 ml of dry tetrahydrofuran, sodium hydride (0.335 g, (ca.60% in mineral oil), 0.0042×2.0 mol) was added. After the bubbling ceased, a solution of 2,6-dichloro-4-dimethylaminopyridine (0.8 g, 0.0042 mol) in 20 ml of dry tetrahydrofuran was added dropwise at room temperature.

After the addition, the resultant solution was stirred for 24 hours under reflux. Then, the solvent was distilled off and the residue was partitioned between chloroform and water. The obtained organic layer was washed successively with aqueous saturated sodium hydrogen carbonate and aqueous saturated sodium chloride, then dried over anhydrous sodium sulfate. After the solvent was distilled off, the residue was purified on a silica gel column to obtain the end product.

Yield: 0.63 g (56%). Solid.
Melting point: 78°–79° C.

$^1$H-NMR (60 MHz, CDCl$_3$, δ): 2.86(6H,s), 5.20(2H,s), 5.73(1H,d,J=2 Hz), 6.15(1H,d,J=2 Hz), 7.0–7.3(3H, complex).

(2) Synthesis of 4-dimethylamino-2-(3-thienylmethyloxy)-6-(meta-trifluoromethylphenoxy)pyridine from the intermediate To a solution of meta-trifluoromethylphenol (1.27 g, 0.0020×4.0 mol) in 20 ml of dry N,N-dimethylacetamide, sodium hydride (0.313 g, (ca.60% in mineral oil), 0.0020×4.0 mol) was added. After the bubbling ceased, a solution of 2-chloro-4-dimethylamino-6-(3-thienylmethyloxy)pyridine (0.526 g, 0.0020 mol) in 20 ml of dry N,N-dimethylacetamide was added dropwise, then CuI (0.186 g, 0.0020×0.5 mol) was added thereto and the resultant solution was stirred for 24 hours at the temperature of 170° to 180° C.

After allowed to cool, the reaction solution was filtered through a glass filter covered with Celite and the filtrate was partitioned between chloroform and water.

The obtained organic layer was washed successively with aqueous saturated sodium hydrogen carbonate and aqueous saturated sodium chloride, then dried over anhydrous sodium sulfate. The solvent was distilled off and the residue was purified on column chromatography (elution solvent: acetonitrile/water=7/3 (v/v), Lobar column, Lichroprep RP-18, 40–63 μm), whereby the end product was obtained.

Yield: 0.26 g (34%). Solid.
Melting point 78°–80° C.

$^1$H-NMR (60 MHz, CDCl$_3$, δ): 2.9(6H,s), 5.0(2H,s), 5.66(1H,d,J=2 Hz), 5.7(1H,d,J=2 Hz), 6.8–7.4(7H, complex).

REFERENCE SYNTHESIS EXAMPLE 1

Synthesis of 2,6-dichloro-4-methoxypyridine used in the Synthesis example 6

To a tetrahydrofuran solution containing methanol (0.37 g, 0.0104×1.1 mol), sodium hydride (0.44 g, (ca.60% in mineral oil), 0.0104×1.05 mol) was added. Then 2,6-dichloro-4-nitropyridine (2.00 g, 0.0104 mol) was added thereto and the mixture was stirred for about 2 hours at room temperature. After it was confirmed that there was no bubbling with the addition of methanol (0.5 g), the mixture was stirred for about 1 hour. The reaction solution was partitioned between ethyl acetate and water. The obtained organic layer was washed successively with aqueous saturated sodium hydrogen carbonate and aqueous saturated sodium chloride, then dried over anhydrous sodium sulfate and concentrated to obtain the end product which was almost pure.

Yield: 1.63 g (88%). Solid.
Melting point: 94°–96° C.

$^1$H-NMR (60 MHz, CDCl$_3$, δ): 3.79(3H,s), 6.70(2H,s).

REFERENCE SYNTHESIS EXAMPLE 2

Synthesis of 2,6-dichloro-4-methylmercaptopyridine (used in the Synthesis example 7)

To a dimethylformamide solution of 2,6-dichloro-4-nitropyridine (2.0 g, 0.0104 mol), a sodium methanethiol solution (4.84 g, (15% aqueous solution), 0.0104×1.0 mol) was added, and the solution was stirred for about 1 hour at room temperature. The reaction solution was partitioned between ethyl acetate and water. The obtained organic layer was washed successively with aqueous saturated sodium hydrogen carbonate and aqueous saturated sodium chloride, then dried over anhydrous sodium sulfate and concentrated. From the concentrate, distillate was collected with a tubular oven at about 170° C. under aspiration (17–18 mmHg) to obtain the end product.

Yield: 1.83 g (91%). Solid.
Melting point: 69°–73° C.

$^1$H-NMR (60 MHz, CDCl$_3$, δ): 2.43(3H,s), 6.82(2H,s).

REFERENCE SYNTHESIS EXAMPLE 3

Synthesis of 2,6-dichloro-4-methylaminopyridine (used in the Synthesis example 9)

2,6-Dichloro-4-nitropyridine (3.0 g, 15.5 mmol) was dissolved in 50 ml of acetonitrile, and an aqueous methylamine solution (3.62 g, (40% aqueous solution), 15.5×3 mmol) was added dropwise thereto. The solution was stirred for 1 hour at room temperature, and 100 ml of water was added thereto. The precipitated solid was filtered off, washed with water, and dried.

Yield: 2.54 g (92.7%). Yellow solid.
Melting point: 194°–196° C.
$^1$H-NMR (60 MHz, CDCl$_3$ +d$_6$DMSO, δ): 2.7(3H,d,J=5 Hz), 6.3 (2H,s). (NH was indefinite.).

REFERENCE SYNTHESIS EXAMPLE 4

Synthesis of 2,6-dichloro-4-dimethylaminopyridine (used in the Synthesis example 10)

To a solution of 4-amino-2,6-dichloropyridine (3.0 g, 18.4 mmol) in 50 ml of dry dimethylformamide, sodium hydride (1.47 g, (ca.60% in mineral oil), 18.4×2 mmol) was added at room temperature. After the bubbling ceased, a solution of methyl iodide (5.2 g, 18.4×2 mmol) in 5 ml of dry dimethylformamide was added dropwise. The resultant solution was stirred for 4 hours at room temperature and the reaction solution was poured into iced water. The precipitated solid was filtered off, washed with water, and dried.

Yield: 3.47 g (99.1%). White solid.
Melting point: 137°–139° C.
$^1$-NMR (60 MHz, CDCl$_3$, δ): 2.9(6H,s), 6.28(2H,s).

The other compounds shown in the Table 1 were also synthesized in a similar manner to that described in any of the above Examples. Properties and NMR data of the obtained compounds are shown in the Table 2.

TABLE 2

| No. | Property | $^1$H-NMR (60 MHz, CDCl$_3$, δ |
|---|---|---|
| I-1 | Oily | 5.05(2H, s), 6.29(1H, d, J=7.9Hz) 6.35(1H, d, J=7.9Hz), 6.6–7.4(7H, complex) 7.41(1H, t, J=7.9Hz) |
| I-2 | Oily | 2.30(3H, s), 5.10(2H, s), 6.21(1H, d, J=7.9Hz) 6.31(1H, d, J=7.9Hz), 6.6–7.3(7H, complex) 7.37 (1H, t, J=7.9Hz) |
| I-6 | Oily | 5.05(2H, s), 6.34(1H, d, J=7.9Hz) 6.38(1H, d, J=7.9Hz), 6.7–7.5(7H, complex) 7.43(1H, t, J=7.9Hz) |
| I-7 | Oily | 2.36(3H, s), 5.09(2H, s) 6.2–6.7(4H, complex), 7.0–7.6(5H, complex) |
| I-14 | Oily | 3.72(3H, s), 4.98(2H, s), 5.8–6.2(2H, complex) 6.6–7.4(3H, Complex), 7.57(3H, s) |
| I-16 | Oily | 3.69 (3H, s), 5.04 (2H, s) 5.95(2H, s), 6.7–7.6(7H, complex) |
| I-17 | Oily | 3.66(3H, s), 5.05(2H, s), 5.90(2H, s) 6.36(1H, t, J=73Hz), 6.6–7.5(7H, complex) |
| I-18 | Oily | 3.70(3H, s), 5.11(2H, s), 5.8–6.2(2H, complex), 6.66(1H, d, J=1.6Hz), 7.00(1H, d, J=1.6Hz) 7.0–7.6(4H, complex) |
| I-19 | Oily | 3.68(3H, s), 5.06(2H, s), 5.7–6.1(2H, complex), 6.48(1H, d, J=3.4Hz), 6.71(1H, d, J=3.4Hz) 6.9–7.5(4H, complex) |
| I-20 | Oily | 2.12(3H, s), 3.68(3H, s), 5.12(2H, s) 5.94(2H, s), 6.66(1H, d, J=5Hz), 7.02(1H, d, J= 5Hz) 7.0–7.5(4H, complex) |
| I-21 | Oily | 2.34(3H, s), 3.66(3H, s), 5.07(2H, s) 5.9–6.1(2H, complex), 6.40(1H, d, J=3.6Hz), 6.53(1H, d, J=3.6Hz), 7.1–7.5(4H, complex) |
| I-23 | Oily | 2.20(3H, s), 2.29(3H, s), 3.69(3H, s), 4.86(2H, s) 5.92(2H, s), 6.39(1H, s), 6.9–7.6(4H, complex) |

Formulation examples and test examples are hereinafter described. Kinds of carriers (diluents) and additives to be used, as well as mixing ratios thereof and active ingredient contents therein may be modified in a broad range.

In each of the formulation examples, the term "parts" is "parts by weight".

FORMULATION EXAMPLE 1

(wettable powder)

| The compound of the present invention | 50 parts |
|---|---|
| Lignin sulfonate | 5 parts |
| Alkyl sulfonate | 3 parts |
| Diatomaceous earth | 42 parts |

The above ingredients were mixed together and ground finely to form a wettable powder. It may be applied after diluted with water.

FORMULATION EXAMPLE 2

(emulsifiable concentrate)

| The compound of the present invention | 25 parts |
|---|---|
| Xylene | 65 parts |
| Polyoxyethylene alkylaryl ether | 10 parts |

The above ingredients were homogeneously mixed to form an emulsifiable concentrate. In may be applied after diluted with water.

FORMULATION EXAMPLE 3

(granule)

| The compound of the present invention | 8 parts |
|---|---|
| Bentonite | 40 parts |
| Clay | 45 parts |
| Lignin sulfonate | 7 parts |

The above ingredients were homogeneously mixed, blended with water and processed into a granular form with an extrusion granulator to give granules.

TEST EXAMPLE 1

(Weed control test by foliage and soil treatments)

Wettable powder of each test compound was prepared as described in the Formulation example 1 and suspended at a predetermined concentration. Thus formed herbicidal solution was applied at an active ingredient rate of 100 g/10 a onto both the soil and the foliage of each plant grown to the 1 to 2 leaf stage. The tested plants were pot-cultivated redroot pigweed (*Amaranthus retroflexus*), wild mustard (*Sinapis arvensis*), sicklepod (*Cassia obtusifolia*), black nightshade (*Solanum nigrum*), velvetleaf (*Abutlion theophrasti*), cleavers (*Galium aparine*) and ivyleafspeedwell (*Veronica hederaefolia*).

On the 14th day after the application, weed control effects were evaluated by the following criterion.

Evaluation rating:

1: less than 25% of weedkilling

2: 25% to less than 50% of weedkilling

3: more than 50% of weedkilling

The results are shown in the Table 3.

TABLE 3

| No. | Dose (q ai/10 a) | Weed[A] | | | | | | |
|---|---|---|---|---|---|---|---|---|
| | | AR | SA | CO | SN | AT | GA | VH |
| I-3 | 100 | 3 | 3 | 3 | 3 | 3 | 3 | 3 |
| I-4 | 100 | 3 | 3 | 3 | 3 | 3 | 3 | 3 |
| I-7 | 100 | 3 | 3 | 3 | 3 | 3 | 3 | 3 |
| I-8 | 100 | 3 | 3 | 3 | 3 | 3 | 3 | 3 |
| I-9 | 100 | 3 | 3 | 3 | 3 | 3 | 3 | 3 |
| I-10 | 100 | 3 | 3 | 3 | 3 | 3 | 3 | 3 |
| I-13 | 100 | 3 | 3 | 3 | 3 | 3 | 3 | 3 |
| I-16 | 100 | 3 | 3 | 3 | 3 | 3 | 3 | 3 |
| I-17 | 100 | 3 | 3 | 3 | 3 | 3 | 3 | 3 |
| I-18 | 100 | 3 | 3 | 3 | 3 | 3 | 3 | 3 |
| I-19 | 100 | 3 | 3 | 3 | 3 | 3 | 3 | 3 |
| I-20 | 100 | 3 | 3 | 3 | 3 | 3 | 3 | 3 |
| I-21 | 100 | 3 | 3 | 3 | 3 | 3 | 3 | 3 |
| I-26 | 100 | 3 | 3 | 3 | 3 | 3 | 3 | 3 |
| I-28 | 100 | 3 | 3 | 3 | 3 | 3 | 3 | 3 |
| I-29 | 100 | 3 | 3 | 3 | 3 | 3 | 3 | 3 |

[A]: AR: *Amaranthus retroflexus*;
SA: *Sinapis arvensis*;
CO: *Cassia obtusifolia*;
SN: *Solanum nigrum*;
AT: *Abutilon theophrasti*;
GA: *Galium aparine*;
VH: *Veronica hederaefolia*.

What is claimed is:
1. A 2-phenoxy-6-thienylmethyloxypyridine derivative represented by the formula (I) :

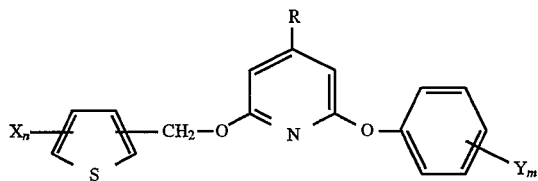

wherein R represents hydrogen, a halogen, cyano, $C_1$–$C_4$ alkyl, $C_1$–$C_4$ alkoxy, $C_1$–$C_4$ alkylthio, $C_1$–$C_4$ haloalkyl, $C_1$–$C_4$ alkylamino, or di ($C_1$–$C_4$) amino;

each X, which may be identical or different if n is greater than 1, represents a halogen, $C_1$–$C_4$ alkyl, $C_1$–$C_4$ alkoxy, $C_1$–$C_4$ alkylthio, or $C_1$–$C_4$ haloalkyl;

each Y, which may be identical or different if m is greater than 1, represents a halogen, $C_1$–$C_4$ alkyl, $C_1$–$C_4$ alkoxy, $C_1$–$C_4$ alkylthio, $C_1$–$C_4$ haloalkyl, $C_1$–$C_4$ haloalkoxy, or $C_1$–$C_4$ haloalkylthio;

m represents an integer of 0 to 5; and n represents an integer of 0 to 3.

2. A compound according to claim 1, wherein Y represents trifluoromethyl, difluoromethoxy, trifluoromethoxy, or trifluoromethylthio; R represents hydrogen, a halogen, cyano, methyl, methoxy, methylthio, methylamino, dimethylamino, or trifluoromethyl; and n represents 0.

3. A herbicidal composition comprising an effective amount of a 2-phenoxy-6-thienylmethyloxypyridine derivative of the formula (I):

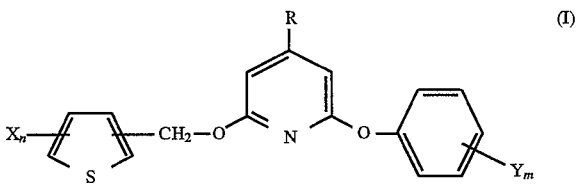

wherein R represents hydrogen, a halogen, cyano, $C_1$–$C_4$ alkyl, $C_1$–$C_4$ alkoxy, $C_1$–$C_4$ alkylthio, $C_1$–$C_4$ haloalkyl, $C_1$–$C_4$ alkylamino, or di($C_1$–$C_4$ alkyl)amino;

each X, which may be identical or different if n is greater than 1, represents a halogen, $C_1$–$C_4$ alkyl, $C_1$–$C_4$ alkoxy, $C_1$–$C_4$ alkylthio, or $C_1$–$C_4$ haloalkyl;

each Y, which may be identical or different if m is greater than 1, represents a halogen, $C_1$–$C_4$ alkyl, $C_1$–$C_4$ alkoxy, $C_1$–$C_4$ alkylthio, $C_1$–$C_4$ haloalkyl, $C_1$–$C_4$ haloalkoxy, or $C_1$–$C_4$ haloalkylthio;

m represents an integer of 0 to 5; and n represents an integer of 0 to 3, and an adjuvant.

4. A herbicidal composition according to claim 3, wherein Y represents trifluoromethyl, difluoromethoxy, or trifluoromethoxy; R represents hydrogen, a halogen, cyano, methyl, methoxy, methylthio, methylamino, dimethylamino, or trifluoromethyl; and n represents 0.

* * * * *